US009916655B2

(12) United States Patent
Stampanoni et al.

(10) Patent No.: US 9,916,655 B2
(45) Date of Patent: Mar. 13, 2018

(54) IMAGE FUSION SCHEME FOR DIFFERENTIAL PHASE CONTRAST IMAGING (71) Applicant: PAUL SCHERRER INSTITUT, Villigen Psi (CH)

(72) Inventors: Marco Stampanoni, Endingen (CH); Zhentian Wang, Brugg (CH)

(73) Assignee: Paul Scherrer Institut, Villigen PSI (CH)

( * ) Notice: Subject to any disclaimer, the term of this patent is extended or adjusted under 35 U.S.C. 154(b) by 148 days.

(21) Appl. No.: 14/896,531

(22) PCT Filed: May 28, 2014

(86) PCT No.: PCT/EP2014/001441
§ 371 (c)(1),
(2) Date: Dec. 7, 2015

(87) PCT Pub. No.: WO2014/194995
PCT Pub. Date: Dec. 11, 2014

(65) Prior Publication Data
US 2016/0125599 A1 May 5, 2016

Related U.S. Application Data (60) Provisional application No. 61/832,343, filed on Jun. 7, 2013.

(51) Int. Cl.
*G06K 9/00* (2006.01)
*G06T 7/00* (2017.01)
(Continued)

(52) U.S. Cl.
CPC ............ *G06T 7/0012* (2013.01); *A61B 6/481* (2013.01); *A61B 6/483* (2013.01); *A61B 6/484* (2013.01);
(Continued)

(58) Field of Classification Search
USPC ........ 382/100, 103, 106–107, 128–134, 153, 382/162–168, 173, 181, 191, 219, 224,
(Continued)

(56) References Cited

U.S. PATENT DOCUMENTS 5,218,649 A * 6/1993 Kundu ...................... G06T 5/20
348/625
9,117,296 B2 * 8/2015 Stampanoni ........... A61B 6/483
(Continued)

FOREIGN PATENT DOCUMENTS

WO 2013014083 A1 1/2013
WO 2013027138 A1 2/2013

OTHER PUBLICATIONS

Stampanoni M et al.: "Toward clinical differential phase contrast mammography: preliminary evaluations and image processing schemes", Journal of Instrumentation, Institute of Physics Publishing, Bristol, GB, vol. 8, No. 5, May 31, 2013 (May 31, 2013), p. C05009, XP020244606.
(Continued)

*Primary Examiner* — Seyed Azarian
(74) *Attorney, Agent, or Firm* — Laurence Greenberg; Werner Stemer; Ralph Locher (57) ABSTRACT

The latest progresses in breast imaging using differential phase contrast techniques pose the question of how to fuse multiple information sources, yielded by absorption, differential phase, and scattering signals, into a single, informative image for clinical diagnosis. It is proposed to use an image fusion scheme based on a multiple-resolution framework. The three signals are first transformed into multiple bands presenting information at different frequencies and then a two-step processing follows: (1) intra-band processing enhances the local signal-to-noise ratio using a novel noise estimation method and context modeling; and (2) inter-band processing weights each band by considering
(Continued)

their characteristics and contributions, and suppressing the global noise level. The fused image, looking similar to a conventional mammogram but with significantly enhanced detail features, is reconstructed by inverse transform. The fused image is compatible with clinical settings and enables the radiologists to use their years of diagnosis experiences in mammography.

15 Claims, 6 Drawing Sheets

(51) Int. Cl.
    *A61B 6/00*         (2006.01)
    *G06T 5/50*         (2006.01)
    *G06K 9/52*         (2006.01)
    *G06T 7/60*         (2017.01)
    *G06T 11/00*       (2006.01)
    *G06T 11/60*       (2006.01)
    *G06T 7/73*         (2017.01)
    *B41M 5/00*       (2006.01)

(52) U.S. Cl.
    CPC ............ *A61B 6/502* (2013.01); *A61B 6/5235* (2013.01); *G06K 9/52* (2013.01); *G06T 5/50* (2013.01); *G06T 7/60* (2013.01); *G06T 7/73* (2017.01); *G06T 11/003* (2013.01); *G06T 11/60* (2013.01); *A61B 6/5258* (2013.01); *G06T 2207/10072* (2013.01); *G06T 2207/10116* (2013.01); *G06T 2207/20052* (2013.01); *G06T 2207/20064* (2013.01); *G06T 2207/20221* (2013.01); *G06T 2207/30068* (2013.01)

(58) Field of Classification Search
    USPC ........ 382/232, 254, 274–276, 286–295, 305; 348/625; 378/4, 21, 28
    See application file for complete search history.

(56) References Cited

U.S. PATENT DOCUMENTS

| 9,299,130 B2 * | 3/2016 | Panetta | G06T 5/002 |
| 9,472,007 B2 * | 10/2016 | Maack | G06T 11/60 |
| 2014/0169653 A1 * | 6/2014 | Maack | G06T 11/60 |
| | | | 382/132 |

OTHER PUBLICATIONS

Zhentian Wang et al.: "Phase-contrast enhanced mammography: A new diagnostic tool for breast imaging", AIP Conference Proceedings, Jan. 1, 2012 (Jan. 1, 2012) pp. 103-106, XP055150837.

Carolina Arboleda et al: "Wavelet-based noise-model driven denoising algorithm for differential phase contrast mammography", Optics Express, vol. 21, No. 9, May 6, 2013 (May 6, 2013), p. 10572, XP055150835.

Grace Chang S et al.: "Spatially Adaptive Wavelet Thresholding with Context Modeling for Image Denoising" IEEE Transactions on Image Processing, IEEE Service Center, Piscataway, NJ, US, vol. 9, No. 9, Sep. 1, 2000 (Sep. 1, 2000), XP011025656.

Z Wang et al.: "Image fusion scheme for differential phase contrast mammography" Journal of Instrumentation, vol. 8, No. 7, Jul. 31, 2013 (Jul. 31, 2013), pp. C07011-C07011, XP055150834.

Zhifeng Huang et al.: "Attenuation-refraction-scattering computed tomographic experimental system with a conventional X-ray tube: System optimization & image fusion", 2009 IEEE Nuclear Science Symposium and Medical Imaging Conference (NSS/MIC 2009), Orlando, FL, USA, IEEE, Piscataway, NJ, USA, Oct. 24, 2009 (Oct. 24, 2009) pp. 2347-2350, XP-031826859.

Revol Vincent et al.: "Noise analysis of grating-based x-ray differential phase contrast imaging", Review of Scientific Instruments, AIP, Melville, NY, US, vol. 81, No. 7, Jul. 27, 2010 (Jul. 27, 2010), pp. 73709-73709, XP012145944.

\* cited by examiner

IMAGE FUSION SCHEME FOR DIFFERENTIAL PHASE CONTRAST IMAGING

BACKGROUND OF THE INVENTION

Field of the Invention

The present invention relates to a method and a system for differential phase contrast imaging in the medical environment using an image fusion scheme.

Phase contrast and scattering-based X-ray imaging can access information which are not detectable in conventional absorption-based methods, and therefore are considered as promising tools to significantly improve medical X-ray imaging. In the last few years, X-ray grating interferometry has been proved to be a suitable technique for both phase contrast and scattering imaging. It can simultaneously measure the absorption contrast (AC) image, the differential phase contrast (DPC) image and the dark-field (scattering) contrast (DFC) images (also called small angle scattering contrast image), providing much richer information of the underlying sample than conventional X-ray radiography. This technique has been first successfully implemented on synchrotron facilities and further on conventional X-ray tubes, paving the road for its broad usage in medical applications.

Among radiological applications, mammography is one of the techniques that may profit significantly from this technique because of the advantages of phase contrast in imaging soft tissue at lower doses and the additional diagnostic values that could be gained from the scattering signals. Recently, a research team domiziled at the PSI presented the first investigation of native, non-fixed whole breast samples using a grating interferometer based on a conventional X-ray tube configuration (MammoDPC). The preliminary results confirmed that this novel technique provides clinically relevant information to complement and improve the diagnosis for mammography.

To evaluate this technology and further apply it in clinical circumstances, a rising question has been how to effectively fuse the AC, DPC, and DFC signals into one single, but more informative image. This image fusion problem is crucial for radiologists to adopt the MammoDPC technique in clinical applications because in practice it can significantly reduce the time for diagnosis and the complexity to interpret the three different physical signals and enable the radiologists to use their multiple years of breast cancer diagnostic experience. Further, the fused image can often provide intuitive, additional clinical information that are not apparent in the single images, and therefore results in more accurate diagnosis and consequent better treatment. It has been shown that RGB or IHS colour-coded image fusion method is an efficient and natural way to represent the three signals and especially suitable for human vision [1]. However so far, it does not comply with conventional gray-level images in mammography which radiologists and medical doctors are used to work with, as well as the high-resolution (grey-level only) clinical monitors.

BRIEF SUMMARY OF THE INVENTION

It is therefore the objective of the present invention to provide a method and a system for an image fusion scheme in differential phase contrast imaging which perfectly fits into the existing diagnostic environment and routines in today's radiologists work.

This objective is achieved according to the present invention by a method and a system for calculated image fusion in medical X-ray imaging, preferably mammography, wherein the absorption data, the differential phase contrast data and the (small-angle) scattering data of the images of the underlying sample are merged by a fusion algorithm into one single, grey-level image with enhanced details.

This fusion strategy merges therefore the three signals into one single grey-level image which has a similar appearance as the conventional mammograms but with significantly enhanced detail features yielded by the DPC and DFC signals. Moreover, to ensure accurate diagnosis, the fusion procedure will neither sabotage the resolution nor increase the noise level. Dramatic differences in noise properties of the three signals have been observed in grating interferometer, which are therefore handled carefully in the fusion algorithm.

In a preferred embodiment of the present invention, the image fusion algorithm is based on a multiple-resolution (MR) framework, where the original image is decomposed into several sub-images containing the information of the original image at different spatial frequencies, preferably Laplacian, wavelets or similar transformations which carry out the decomposition. The decomposition therefore emphasizes the contribution of the DPC and the DFC signals to the fused image since the most interesting contributions of the DPC and DFC signals materializes rather in the high frequency domain than the contribution of AC signal which contributes rather in the low frequency domain.

Preferably, absorption data AC, the differential phase contrast data DPC and the (small-angle) scattering data DFC are obtained from X-ray investigations based on grating-based interferometry, analyzer-crystal-based imaging, coded aperture imaging or any imaging technique that record these three images. It has to be noted that the terms absorption data, absorption image, absorption signal rather mean the same, namely the intensities of the X-ray imaging for the absorption caused alteration of the incident x-ray beam. Accordingly, this also applies to the differential phase contrast and the (small-angle) scattering.

As mentioned above, the fusion algorithm will focus on generally spoken three main steps:
a) step 1: the absorption, differential phase contrast and (small-angle) scattering images are transformed into a MR domain (for instance, wavelet domain) consisting of multiple levels (s denotes the level index), each level containing several sub-bands (o denotes the band index);
b) step 2: the sub-band images are processed and merged in the MR domain; and
c) step 3: the merged image is reconstructed by the inverse MR transform.

An advantageous feature for the execution of step 2 can be achieved when step 2 includes either an intra-band, or inter-band or both processing, wherein the fused sub-band $F_l(\hat{t})$ can be generally expressed by $$F_l(\hat{t}) = \sum_{X \in [AC, DPC, DFC]} wn_{X,l} \cdot wb_{X,l} \cdot w_{X,l}(\hat{t}) \cdot D_{X,l}(\hat{t}),$$

where X represents one of the possible image types: the absorption contrast (AC), the differential phase contrast (DPC) or the dark-field contrast (DFC); $D_{X,l}(\hat{t})$ represents the unprocessed coefficients of band l; l denotes the pair (s,o), indicating a certain band at level s and of band o. $o \in \{HL, LH, HH\}$ when wavelet transform is used for the decomposition. $\hat{t}=(m,n)$ denotes the 2D coordinates in the sub-band image, and wherein the intra-band processing, which is represented by $w_{X,l}(\hat{t})\cdot D_{X,l}(\hat{t})$, assigns a weighting factor $w_{X,l}(\hat{t})$ to each coefficient within band l with the purpose to increase the local signal-to-noise ratio (SNR); and wherein the inter-band processing gives a global weighting factor $wn_{X,l}\cdot wb_{X,l}$ to each band with the purpose of selecting useful information according to the image characteristics and constraining the global noise level; specifically, $wb_{X,l}$ denotes the band selection weighting factor and $wn_{X,l}$ denotes the noise constraint weighting factor.

Preferably, the weighting factor $w_{X,l}(\hat{t})$ in the intra-band processing is given by $$w_{X,l}(\hat{t}) = \phi\left(\frac{\sigma_{Sw}^{(s,o)}(\hat{t})}{\sigma_{Nw}^{(s,o)}(\hat{t})}\right),$$

where $\phi(x)$ is a linear function which normalizes x into a certain range wherein the ratio $$\frac{\sigma_{Sw}^{(s,o)}(\hat{t})}{\sigma_{Nw}^{(s,o)}(\hat{t})}$$

is defined as the local SNR for $D_{X,l}(\hat{t})$ and $\sigma_{Sw}^{(s,o)}(\hat{t})$ and $\sigma_{Nw}^{(s,o)}(\hat{t})$ denote the local estimated signal strength and the standard noise variance, respectively; for simplicity, the superscript (s,o) of $\sigma_{Sw}^{(s,o)}(\hat{t})$ and $\sigma_{Nw}^{(s,o)}(\hat{t})$ is omitted; $\sigma_{Sw}(\hat{t})$ and $\sigma_{Nw}(\hat{t})$ are used in the following claims; the three images types and their sub-bands are treated in the same way, so the subscript X,l is also dropped.

In the fusion algorithm, the noise has to be watched attentively since an incorrect handling of the noise could have the potential to corrupt the entire method. Therefore, as a further preferred embodiment of the present invention, the local standard noise variance $\sigma_{Nw}(\hat{t})$ in the MR domain is estimated using the prior knowledge of the spatial pixel-wise noise variance $\sigma_{Ns}(\hat{t})$ in the original image:

$$[\sigma_{Nw}^{(s,o)}(\hat{t})]^2 \approx \frac{1}{2\pi}\int_{-\pi}^{\pi}|H^{(s,o)}(\hat{\omega})|^2 \cdot |A(\hat{\omega})|^2 e^{j\hat{\omega}\hat{t}}\,d\hat{\omega},$$

where $H^{(s,o)}(\omega)$ is the frequency response of the cascaded wavelet filters at scale s and orientation o, for example $H^{(s,o)}(\omega)=\Pi_{i=0}^{s-1}H(2^i\omega)G(2^s\omega)$, where $G(\omega)$ and $H(\omega)$ are the scaling and wavelet filters, respectively wherein the standard wavelet notation has been used:
$A(\hat{\omega})$ is the Discrete-time Fourier transform (DTFT) of $\sigma_{Ns}(\hat{t})$, that is $$A(\hat{\omega})=\int \sigma_{Ns}(\hat{t})e^{-j\hat{\omega}\hat{t}}d\hat{t};$$

$\sigma_{Ns}(\hat{t})$ is measured and/or calculated in advance.

Preferably, the local signal strength $\sigma_{Sw}(\hat{t})$ represents the weight of the coefficient $D(\hat{t})$;
$\sigma_{Sw}(\hat{t})$ is the local $l_p$ norm of the N neighbor coefficients of $D(\hat{t})$, which is $$\sigma_{Sw}(\hat{t}) = \left(\sum_{\hat{t}\in N}[D(\hat{t})]^p\right)^{1/p},$$

where $D(\hat{i})$ may include $D(\hat{t})$ itself or neighbor coefficients from its parent band (s−1,o) or son band (s+1,o); a dedicated estimation of $\sigma_{Sw}(\hat{t})$ is achieved by Context Modeling, where $\sigma_{Sw}(\hat{t})$ is determined as following:

i) a context $Z(\hat{t})$ is assigned to each coefficient $D(\hat{t})$, which indicates the significance of the coefficient and is defined as a weighted average of the absolute values of the N neighbors of $D(\hat{t})$: $Z(\hat{t})=w^T u_{\hat{t}}$, where w and $u_{\hat{t}}$ are the vectorized N×1 weighting factor and the vectorized absolute values of the N neighbor coefficients;

ii) the weighting factor w is statistically obtained by least-square (LS) estimation through the whole sub-band:

$$w=(U^T U)^{-1} U^T |D|,$$

where U is a M×N matrix with each row being $u_{\hat{t}}^T$ for all $\hat{t}$ and D is the M×1 vector containing all the coefficients $D(\hat{t})$. M is the number of coefficients in the sub-band;

after $Z(\hat{t})$ is decided for each coefficient, coefficients whose contexts $Z(\hat{t})$ are close in value are located and sorted. Let $B_t$ denotes the set of coefficients $\{D(\hat{t})\}$ whose context falls in a similar value range. Those coefficients are considered to have similar significances and their standard variance $\sigma_{Sw}$ gives a measurement of the significance, $$\sigma_{Sw}(\hat{t}) = \sqrt{\max\left(\frac{1}{L}\sum_{B_t}D(\hat{t})^2 - \sigma_{Nw}^2(\hat{t}),\,0\right)},$$

where L is the number of the coefficients in $B_t$.

Further, the band selection weighting factors is $$wb_{AC,l}(s) = \frac{1}{1+\eta_{AC}\left(\frac{s}{S}\right)^2},$$

$$wb_{DPC,l}(s) = \begin{cases} \dfrac{\eta_{DPC}\left(\frac{s-s_0}{S}\right)^2}{1+\left(\frac{s-s_0}{S}\right)^2}, & s > s_0 \\ 0, & s \leq s_0 \end{cases},$$

$$wb_{DFC,l}(s) = \begin{cases} \dfrac{\eta_{DFC}\left(\frac{s-s_0}{S}\right)^2}{1+\left(\frac{s-s_0}{S}\right)^2}, & s > s_0 \\ 0, & s \leq s_0 \end{cases},$$

where S is the maximal decomposition level and s=0, 1, . . . , S is the level index; for multiple sub-bands within a certain level, the same weighting factor is used; $\eta_{AC}$, $\eta_{DPC}$ and $\eta_{DFC}$ are the image type related constants controlling the values of the weighting factors and therefore weighting the contributions of each image type to the fusion image; and $s_0$ represents a threshold frequency.

Furthermore, the global noise constraint weighting factors are inversely proportional to the average noise level of the sub-band; for instance, $$wn_{AC,l} = \frac{1/\overline{\sigma}_{AC,l}}{1/\overline{\sigma}_{AC,l} + 1/\overline{\sigma}_{DPC,l} + 1/\overline{\sigma}_{DFC,l}}$$

$$wn_{DPC,l} = \frac{\overline{\sigma}_{AC,l}}{\overline{\sigma}_{DPC,l}} \times wn_{AC,l}$$

$$wn_{DFC,l} = \frac{\overline{\sigma}_{AC,l}}{\overline{\sigma}_{DFC,l}} \times wn_{AC,l}$$

where $\overline{\sigma}_{AC,l}$ is the average noise variance of AC image at band l, $$\overline{\sigma}_{AC,l} = \sqrt{\frac{1}{N}\sum \sigma_{Nw}^2(i)};$$

and
for the DPC and DFC image, $\overline{\sigma}_{DPC,l}$ and $\overline{\sigma}_{DFC,l}$ are decided in the same way.

According to a further preferred embodiment of the present invention, the absorption data, the differential phase contrast data and small-angle scattering data were obtained from an arrangement for X-rays, in particular hard X-rays, for obtaining quantitative X-ray images from a sample, comprising:

a. an X-ray source;
b. three gratings or at least two gratings;
c. a position-sensitive detector with spatially modulated detection sensitivity having a number of individual pixels;
d. means for recording the images of the detector;
e. means for evaluating the intensities for each pixel in a series of images, in order to identify the characteristics of the object for each individual pixel as an absorption dominated pixel and/or a differential phase contrast dominated pixel and/or an X-ray scattering dominated pixel and for executing the fusion algorithm;
f. wherein the series of images is collected by continuously or stepwise rotating from 0 to $\pi$ or $2\pi$ either the sample or the arrangement and the source relative to the sample.

In this context of the afore-mentioned embodiment, the arrangement for X-rays can take the images either according to the so-called "near field regime" or according to the "Talbot-regime", wherein preferably for the near-field-regime operation, the distance between the gratings (G1, G2) is chosen freely within the regime, and for the Talbot-regime the distance is chosen according to $$D_{n,sph} = \frac{L \cdot D_n}{L - D_n} = \frac{L \cdot n \cdot p_1^2 / 2\eta^2 \lambda}{L - n \cdot p_1^2 / 2\eta^2 \lambda}$$

where $n = 1, 3, 5 \ldots$ , and $$\eta = \begin{cases} 1 & \text{if the phase shift of } G_1 \text{ is } (2l-1)\frac{\pi}{2}, \quad p_2 = \frac{L + D_{n,sph}}{L} p_1 \\ 2 & \text{if the phase shift of } G_1 \text{ is } (2l-1)\pi, \quad p_2 = \frac{L + D_{n,sph}}{L} \frac{p_1}{2} \end{cases},$$

where l=1, 2, 3, $D_n$ is an odd fractional Talbot distance when the parallel X-ray beam is used, while $D_{n,sph}$ is that when the fan or cone X-ray beam is used, L is the distance between the source (X-ray) and the first grating (G1).

Typically, in the grating structure of the arrangement for X-rays a first granting is a line grating either as an absorption grating or a phase grating, wherein the phase grating is a low absorption grating but generating a considerable X-ray phase shift, the latter preferably of $\pi$ or odd multiples thereof. Additionally, a second grating (G2) is a line grating having a high X-ray absorption contrast with its period being the same as that of the self image of the first grating; the second grating being placed closely in front of the detector, or integrated in it, with its lines parallel to those of the first grating.

The phase stepping with this arrangement for X-rays can be preferably performed by the shift of one grating with respect to the others gratings in a direction perpendicular to the orientation of the grating lines of the gratings.

For performing a tomographic reconstruction of the images, the fusion protocol in the fusion algorithm is applied to multiple angular projections. The presented fusion protocol is applied to tomographically reconstructed slices

BRIEF DESCRIPTION OF THE SEVERAL VIEWS OF THE DRAWING

Preferred embodiment of the present invention are hereinafter described in more detail with reference to the attached drawings wherein.

DESCRIPTION OF THE INVENTION

According to the present invention, a method and a system for calculated image fusion in medical imaging is disclosed. Presently, an image fusion scheme for differential phase contrast mammography based on the multiple-resolution (MR) method is hereinafter discussed in more detail. The framework using MR method for image fusion has been established by G. Piella [2]. It follows a "decomposition—processing and fusing—reconstruction" style. However for a particular application, like MammoDPC here, principles for the 'processing and fusing' should be explored and designed. The proposed fusion scheme handles the three signals differently with particular care on adding more "signals" than "noises". The AC, DPC, and DFC signals are first transformed into multiple levels and bands, which represent image information at different scales and frequencies, using wavelets decomposition. Then a two-step processing follows: First, an intra-band processing enhances the local signal-to-noise ratio (SNR) and features using a novel noise estimation method to model the noise and the context modeling to model the signal. In the second step, an inter-band processing weights each band by considering their characteristics and contributions, as well as suppressing the global noise level. High frequency components of DPC and DFC images are preferred according to prior diagnostic knowledge while the information of the AC image is well kept. The resulting fusion image has similar appearance as conventional mammogram but significantly enhanced detail features, and the noise level is maintained at the same time.

Fundamentals of MammoDPC Method

Figure 1:
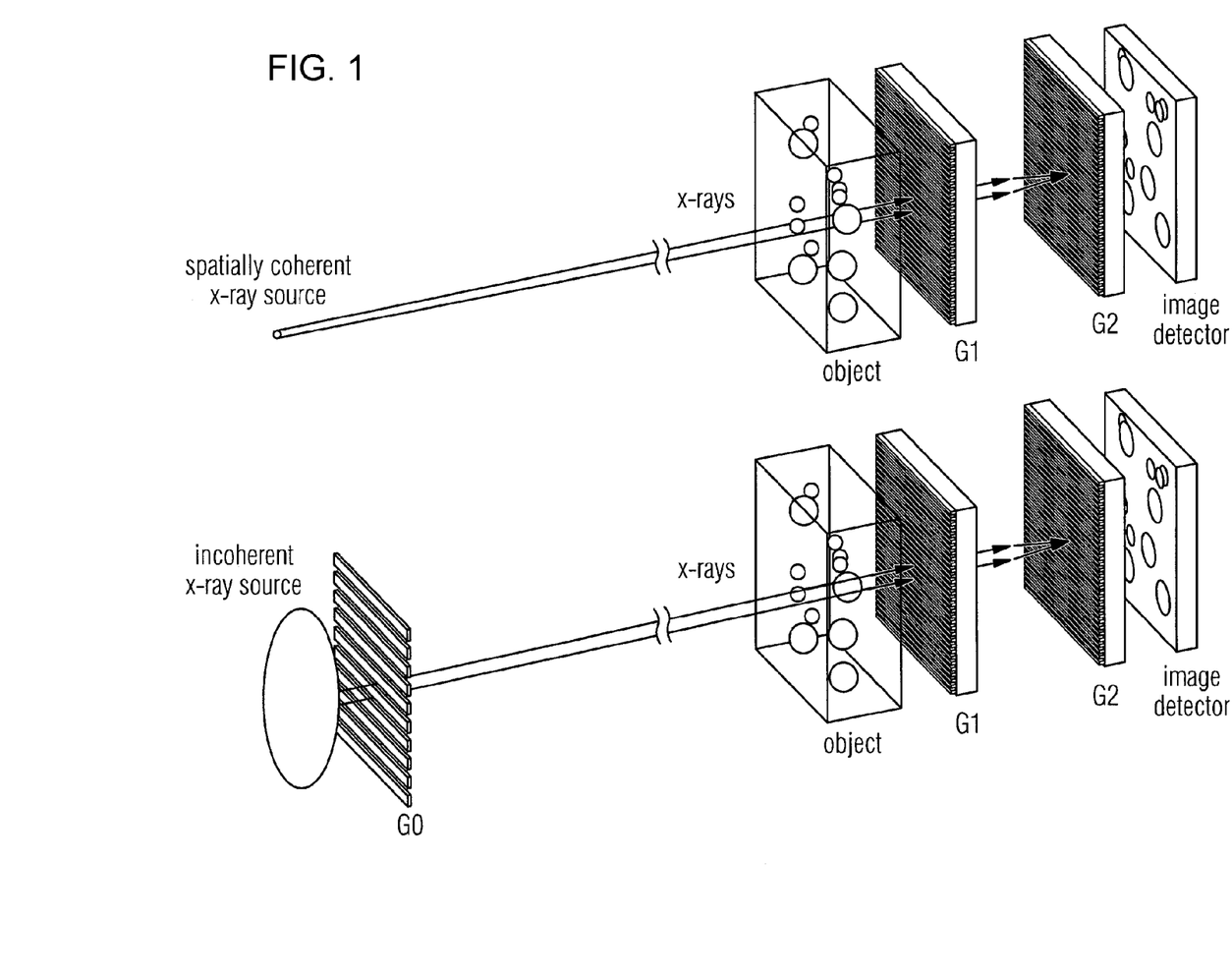
FIG. 1 shows schematically the set-up of a typical grating-based x-ray interferometer.

The principle of grating interferometry for differential phase contrast imaging has been well established in the past few years. Briefly speaking, the system is usually composed of an X-ray tube, a three-grating interferometry, and a 2D detector as shown in FIG. 1. FIG. 1 shows a two-gratings set-up (top) and three-gratings set-up (bottom) for X-ray imaging as for example disclosed in the European Patent applications EP 2 400 891 A1 and EP 1 887 936 A1 which are herewith incorporated by reference.

Image Formation

During the data acquisition, one of the gratings is moved perpendicular to the grating lines within at least one gratings period (phase stepping approach). For each pixel on the detector, a quasi-sine intensity curve is recorded. The AC, DPC, and DFC signals are obtained by an information retrieving algorithm operating on phase stepping curves with and without the object.

The phase stepping curve can be approximately expressed by $$I_{Det}(x,y) \approx a_0(x,y) + a_1(x,y)\sin\left[2\pi\frac{n}{N_{ps}} + \Phi(x,y)\right], \quad (1)$$

where $N_{ps}$ is the number of phase steps, n is the index of the step.

Then the AC, DPC, and DFC images are defined as:

$$AC = -\ln T = -\ln\left(\frac{a_{0,obj}}{a_{0,bg}}\right), \quad (2)$$

$$DPC = \frac{1}{\pi}(\Phi_{obj} - \Phi_{bg}),$$

$$DFC = -\ln V = -\ln\left(\frac{a_{1,obj}}{a_{0,obj}} \cdot \frac{a_{0,bg}}{a_{1,bg}}\right).$$

Signals from the scans with and without object (background scan) are labeled by "obj" and "bg", respectively. It follows that ranges of the recorded signals are AC∈[0 ∞], DPC∈[−1 1], DFC∈ [0 ∞]. T and v are the defined as the transmission image and visibility degradation image which will be used in next section.

Noise Properties

Although the three signals are obtained simultaneously, their intrinsic noise properties are different, which means that they cannot be treated equally in the image fusion process. With a fine-tuned system, the quantum noise on the detector is considered to be the main noise source. In this case, the spatial pixel-wise noise variances could be calculated and measured based on error propagation:

$$\sigma^2_{AC} = \frac{f^r}{N_{ps}a_o^r}\left(1 + \frac{f^s}{f^r} \cdot \frac{1}{T}\right)\overline{T}^2, \quad (3)$$

$$\sigma^2_{DPC} = \frac{f^r}{2\pi^2 v^2 N_{ps}a_o^r}\left(1 + \frac{f^s}{f^r} \cdot \frac{1}{TV^2}\right),$$

$$\sigma^2_{DFC} = \frac{f^r}{v^2 N_{ps}a_o^r}\left[v^2\left(1 + \frac{f^s}{f^r} \cdot \frac{1}{T}\right) + 2\left(1 + \frac{f^s}{f^r} \cdot \frac{1}{TV^2}\right)\right]\overline{V}^2,$$

where $\overline{T}$ and $\overline{V}$ are the mean intensity of the transmission image and visibility degradation image for one pixel as defined in Eq. (2), respectively. $a_o^r$ is the mean intensity of the phase stepping curve without object. v is the visibility at that pixel which can be measured with a background scan. $f^r$ and $f^s$ are noise related coefficients with and without object, which could be measured Error! Reference source not found. v, $f^r$ and $f^s$ are known constants for a tuned system.

The noise variances of DPC and DFC images are generally larger than the absorption image. Considering the possible existences of other noise sources, this noise estimation is considered to be optimistic. However, it could provide useful prior knowledge for post-processing especially because the spatial distribution of the noise is taken into account. In order to use this knowledge in the MR image fusion scheme, one needs to transform the spatial noise variances into the MR domain which will be discussed later.

Additional Diagnostic Values

Figure 2:
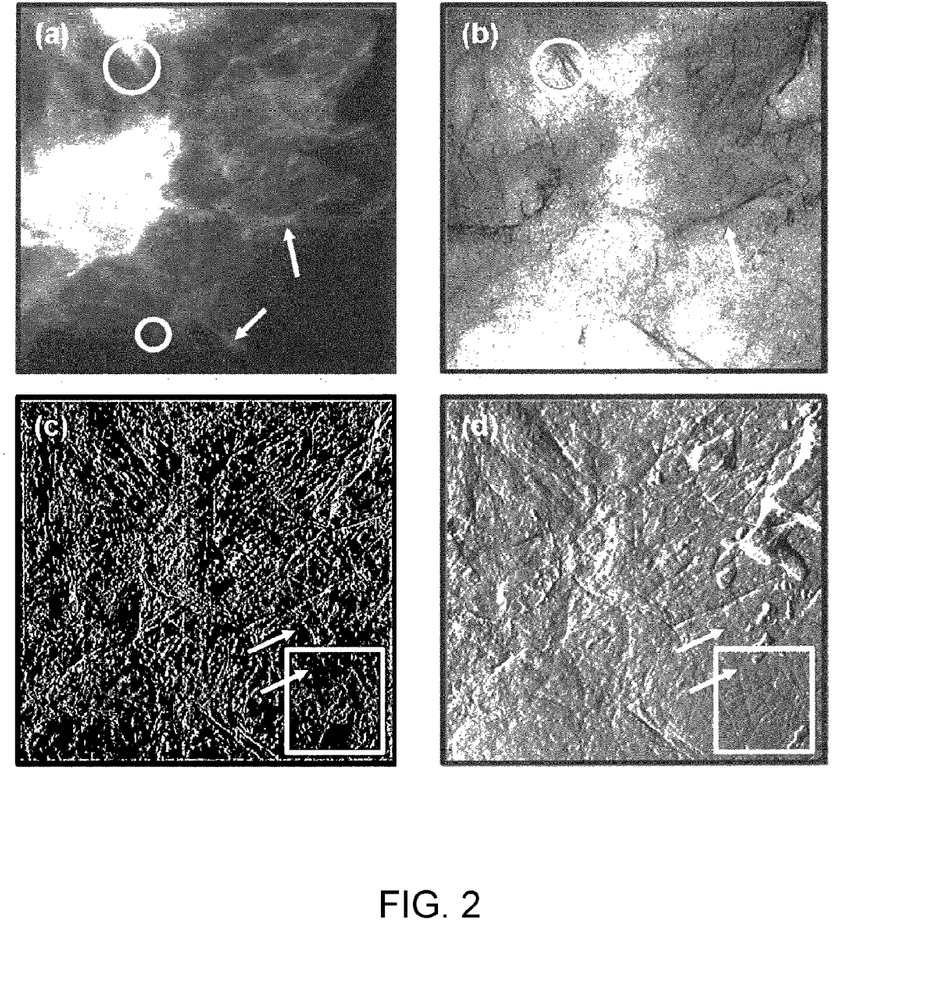
FIG. 2 shows a MammoDPC images for an ROI close to a carcinoma; (a) is the AC image, (b) is the DFC image and (c) is the derivative of the AC image, for fair comparison with the DPC image; (d) represents the DPC image.

Image fusion schemes for MammoDPC should be driven by the additional diagnostic values from the DPC and DFC images. For the DPC image, the main gain is given by the high spatial frequency components of it because the differential phase signal is generally sensitive to the edges at tissues interfaces. The DFC image, on the other hand, contributes greatly in enhancing microcalcifications and fibrous connective tissue visualization. An example is illustrated in FIG. 2. Both DPC and DFC images provide additional and complementary information to the AC image. Besides, DPC image has the potential to distinguish a type of malignant conversion and its extension within normal breast tissue. The advantages of DFC image in imaging microcalcifications and fibrous tissue can play an important role in early breast cancer detection because both microcalcifications and fibrous tissue are related to the development of malignant lesions. From the point of view of image processing, those detail features (edges, microcalcifications and fibrous structures) belong to the high frequency components of the images.

Therefore, in the proposed image fusion scheme, it is aimed at taking preferable high frequency information from DPC and DFC, whereas low frequency information is mostly taken from AC.

FIG. 2 shows a MammoDPC images for an ROI close to a carcinoma. Part (a) shows the AC image; part (b) is the DFC image; and part (c) is the derivative of the AC image, for fair comparison with the DPC image. Part (d) represents the DPC image. The fibrous tissues which are hardly seen in the AC image is highly enhanced, visualized and distinguished in the DFC image as indicated by the arrows and circles in (a) and (b). The DPC image is sensitive to the edges and also provided additional detail features which can not be seen in the AC image as demonstrated in the red rectangular in (c) and (d).

Figure 3:
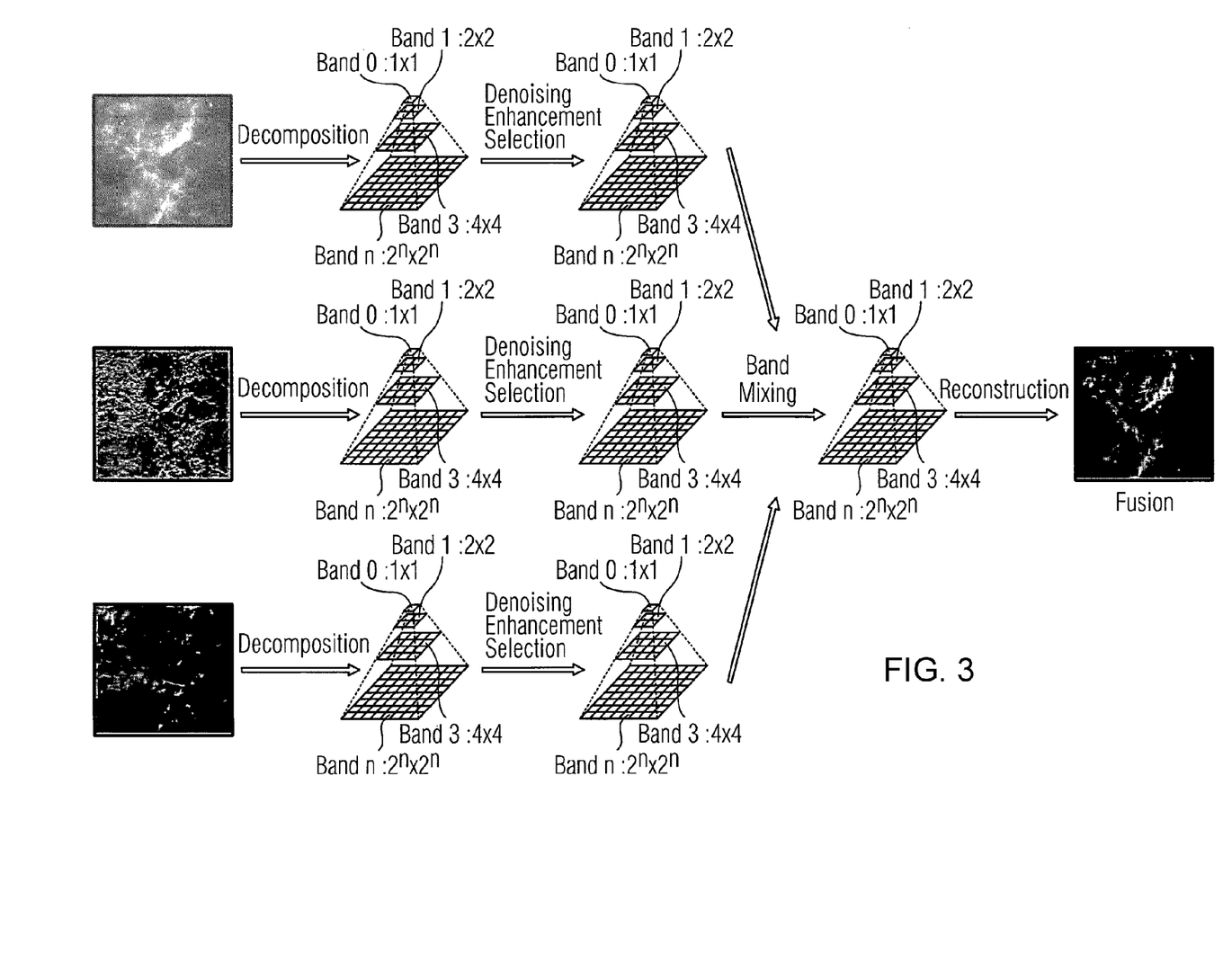
FIG. 3 illustrates the principle of the MR image fusion framework.

In the following the image fusion scheme for MammoDPC is explained in more detail. The principle of the multiple resolution (MR) framework is illustrated in FIG. 3. Generally speaking, the framework includes three steps:

Step 1: The images are first transformed into the MR domain, consisting of multiple levels. Each level might contain several sub-bands depending on the decomposition methods, e.g. Laplacian decomposition or wavelet transform. Each sub-band contains the information of the original image at a different spatial frequency.

Step 2: The band images are then processed and merged within the transformed domain according to the peculiarities of the application.

Step 3: The fusion image is reconstructed by inverse MR transform.

The present scheme therefore mainly acts at the level of Step 2, including an intra- and an inter-band processing, while using a standard wavelet transform at Step 1 and 3.

Many decomposition methods have been studied and are used in various applications. Different types of wavelets, with different properties, could have been used, however this is not a subject for the discussion in this patent application. Instead, a general fusion scheme is proposed for the particular application here, namely, differential phase contrast mammography.

Another advantage of the MR method worth mentioning is that both denoising and contrast enhancement, two common processing steps in radiography, can be applied easily within the same framework, providing the possibility to further improve the fusion result according to the requirements set by the radiologists.

As mentioned earlier, FIG. 3 illustrates the principle of the MR image fusion framework. Images are first decomposed into multiple bands (corresponding to image information at different resolution) and those bands are processed and merged according to the applications. The fusion image is finally reconstructed by inverse transform.

Intra-Band Processing

The intra-band processing is designed to increase local SNR (signal noise resolution). A weighting factor is assigned to each wavelet coefficient:

$$I_{AC,l}(\hat{t}) = w_{AC,SNR}(\hat{t}) \times D_{AC,l}(\hat{t})$$

$$I_{DPC,l}(\hat{t}) = w_{DPC,SNR}(\hat{t}) \times D_{DPC,l}(\hat{t})$$

$$I_{DFC,l}(\hat{t}) = w_{DFC,SNR}(\hat{t}) \times D_{DFC,l}(\hat{t}) \quad (4)$$

where $D_{AC,l}(\hat{t})$ represents the original coefficients of band l in the wavelet domain for the AC image. l denotes the pair (s,o), indicating a certain band at scale s and orientation $o \in \{HL, LH, HH\}$. $\hat{t}=(m,n)$ denotes the 2D coordinates of a given coefficient in wavelet domain. The same notation rules apply to DPC and DFC images.

Here, the DPC image is taken as an example. The weighting factor is given by:

$$w_{DPC,SNR}(\hat{t}) = \phi\left(\frac{\sigma_{Sw}(\hat{t})}{\sigma_{Nw}(\hat{t})}\right), \quad (5)$$

where $\phi(x)$ is a linear normalized function which normalizes the ratio $$\frac{\sigma_{Sw}(\hat{t})}{\sigma_{Nw}(\hat{t})}$$

into the range for a given band. Too large $w_{DPC,SNR}(\hat{t})$ is observed to cause obvious artifacts in the fusion image. To keep the information from the AC image, it's not necessary to process $D_{AC,l}(\hat{t})$. Therefore $w_{AC,SNR}(\hat{t})$ could be fixed to 1.

The goal now is how to estimate the "signal term" $\sigma_{Sw}(\hat{t})$ and the "noise term" $\sigma_{Nw}(\hat{t})$ in the wavelet domain.

Noise Estimation

In order to use the spatial noise information (Eq. (3)) within the MR framework, the expressions of the noise variances in the wavelet domain need to be deducted. Without loss of generality, an additive noise model is assumed with known variance for each pixel, with the noises not being spatially correlated and having local stationary property. The noise at position $\hat{t}$ can be modeled by a standard, white Gaussian noise process $\epsilon(\hat{t})$:

$$n(\hat{t}) = \sigma_{Ns}(\hat{t}) \cdot \epsilon(\hat{t}), \quad (6)$$

where $\sigma_{Ns}(\hat{t})$ is the known standard noise variance in the spatial domain as expressed by Eq. (3). $n(\hat{t})$ is a real-value, zero mean random process. Note $A(\hat{\omega})$ as the Discrete-time Fourier transform (DTFT) of $\sigma_s(\hat{t})$, $$\sigma_{Ns}(\hat{t}) = \frac{1}{2\pi} \int_{-\pi}^{\pi} A(\hat{\omega}) e^{j\hat{\omega}\hat{t}} d\hat{\omega}. \quad (7)$$

Equation (6) now turns into $$n(\hat{t}) = \frac{1}{2\pi} \int_{-\pi}^{\pi} A(\hat{\omega}) e^{j\hat{\omega}\hat{t}} dF(\hat{\omega}), \quad (8)$$

with $F(\hat{\omega})$ being the DTFT of $\epsilon(\hat{t})$.

The spatial noise variance could be therefore expressed by $$[\sigma_{Ns}(\hat{t})]^2 = E[n(\hat{t}) \cdot n(\hat{t})] \quad (9)$$

$$= \left(\frac{1}{2\pi}\right)^2 \int_{-\pi}^{\pi}\int_{-\pi}^{\pi} E[dF(\hat{\omega}_1)dF(\hat{\omega}_2)] A(\hat{\omega}_1) A(\hat{\omega}_2) e^{j\hat{\omega}_1 \hat{t}} e^{j\hat{\omega}_2 \hat{t}}$$

$$= \left(\frac{1}{2\pi}\right)^2 \int_{-\pi}^{\pi}\int_{-\pi}^{\pi} E[dF(\hat{\omega}_1)dF(\hat{\omega}_2)] A^*(\hat{\omega}_1) A(\hat{\omega}_2) e^{-j\hat{\omega}_1 \hat{t}} e^{j\hat{\omega}_2 \hat{t}}$$

$$= \frac{1}{2\pi} \int_{-\pi}^{\pi} A^*(\hat{\omega}) A(\hat{\omega}) e^{j\hat{\omega}\hat{t}} d\hat{\omega}$$

$$= \frac{1}{2\pi} \int_{-\pi}^{\pi} |A(\hat{\omega})|^2 e^{j\hat{\omega}\hat{t}} d\hat{\omega}$$

Here, the fact is used that $n(\hat{t})$ is a real-value process, $A(\hat{\omega}) = A^*(-\hat{\omega})$ and the sign of $\hat{\omega}_1$ is changed for integration. Also, $E[dF(\hat{\omega}_1)dF(\hat{\omega}_2)] = 2\pi\delta(\hat{\omega}_1 - \hat{\omega}_2) d\hat{\omega}_1 d\hat{\omega}_2$ because $F(\hat{\omega})$ has orthogonal increments due to the white noise process.

Following the same procedure, let $H^{(s,o)}(\omega)$ be the frequency response of the cascaded wavelet filters at scale s and orientation o, for example $H^{(s,o)}(\omega) = \Pi_{i=0}^{s-1} H(2^i \omega) G(2^s \omega)$, where $G(\omega)$ and $H(\omega)$ are the scaling and wavelet filters, respectively. The wavelet domain noise variance at scale s and orientation o is approximately given by:

$$[\sigma_{Nw}^{(s,o)}(\hat{t})]^2 = E[n_w(\hat{t}) \cdot n_w(\hat{t})] \quad (10)$$

$$\approx \frac{1}{2\pi} \int_{-\pi}^{\pi} |H^{(s,o)}(\hat{\omega})|^2 \cdot |A(\hat{\omega})|^2 e^{j\hat{\omega}\hat{t}} d\hat{\omega}$$

The connection between the spatial noise variance and the noise variance in the wavelet domain is setup by Eq. (7) and Eq. (10). For simplicity, for now on, the superscript (s,o) is omitted, $\sigma_{Nw}(\hat{t})$ is used in the following sections.

Signal Estimation

To optimally fuse the DPC and DFC images into the AC image, the essential step is to extract all the informative features from them. Ideally, those features need to be decided by diagnostic practices. However, at this stage, a focus is laid on keeping important features by modeling, which can be considered as "blind signal estimation".

The signal is estimated using context modeling (CM), which is a powerful tool and has been effectively used in data compressing and image denoising. It takes into account the naturally, spatially varying characteristics of an image. The fundamental idea is to group pixels of similar nature but not necessarily spatially adjacent in the wavelet domain, and then gather statistical information from those pixels. In our MammoDPC, the images have an average size larger than 5000×4000 pixels, therefore the statistics can be considered to be robust.

For each coefficient $D(\hat{t})$ in the wavelet domain (treating the three images in the same way, so the subscript is dropped in the following), a context $Z(\hat{t})$ is assigned to it, which indicates the significance of the coefficient:

$$Z(\hat{t}) = w^T u_t,  \quad (11)$$

where $Z(\hat{t})$ is defined as a weighted average of the absolute values of its p neighbors, and w and $u_t$ are the vectorized p×1 weighting factor and the absolute values of the neighbor coefficients.

The weighting factor w is obtained by least-square (LS) estimation in the sub-band:

$$w = (U^T U)^{-1} U^T |D|, \quad (12)$$

where U is a N×p matrix with each row being $u_t^T$ for all $\hat{t}$ and D is the N×1 vector containing all the coefficients $D(\hat{t})$. N is the number of coefficients in the sub-band. In our implementation, nine neighbors are used, eight of which are the neighborhood pixels in the same band, and the other one is from the parent band.

After $Z(\hat{t})$ is decided for each coefficient, the variance of the random variable $D(\hat{t})$ is estimated from other coefficients whose context variables are close in value to $Z(\hat{t})$. Coefficients whose contexts $Z(\hat{t})$ are similar are located by applying a moving window on the sorted $Z(\hat{t})$. Let $B_t$ denote the set of points $\{D(\hat{t})\}$ whose context falls in the moving windows. Those coefficients are considered to have similar significances and their standard variance $\sigma_{Sw}$ is calculated:

$$\sigma_{Sw}(\hat{t}) = \sqrt{\max\left(\frac{1}{L}\sum_{B_i} D(\hat{t})^2 - \sigma_{Nw}^2(\hat{t}), 0\right)}, \quad (13)$$

where L is the number of the coefficients in the moving window and $\sigma_{Nw}^2(\hat{t})$ is the pixel-wise noise variance discussed above.

Inter-Band Processing

In this procedure, instead of weighting each coefficient, a global weighting factor is assigned to each band with the purpose to constrain the global noise level and select useful information according to the image characteristics.

The weighting scheme is given by $$F_l = wn_{AC,l} \times wb_{AC,l} \times I_{AC,l} + wn_{DPC,l} \times wb_{DPC,l} \times I_{DPC,l} + wn_{DFC,l} \times wb_{DFC,l} \times I_{DFC,l}, \quad (14)$$

where wb denotes the band selection weighting factor and wn denotes the noise constraint weighting factor and will be introduced in the following section. $I_{AC,l}$, $I_{DPC,l}$ and $I_{DFC,l}$ are the band images after the intra-band processing.

Band Selection

As mentioned above, the higher frequency components of DPC and DFC images are preferred by the present fusion scheme according to the invention. To make sure that the fusion image looks similar to the AC image, the "zero" frequency (LL band) and their low frequency components are not used. This ensures that the histogram of the fusion image does not change dramatically from that of the AC image.

To weight the bands, the ideal weighting factors should be selected by evaluating the amount of useful information contained in the sub-band. This requires practical methods to extract clinical-relative features. We initially apply a weighting scheme which is a heuristic generalization of our Fourier-domain fusion method and extend it to fuse the DFC image. Low frequency components of DPC and DFC images are not used or suppressed while high frequency components of them are preferred.

The band selection weighting factors are given by $$wb_{AC}(s) = \frac{1}{1 + \eta_{AC}\left(\frac{s}{S}\right)^2}, \quad (15)$$

$$wb_{DPC}(s) = \begin{cases} \dfrac{\eta_{DPC}\left(\frac{s-s_0}{S}\right)^2}{1 + \left(\frac{s-s_0}{S}\right)^2}, & s > s_0, \\ 0, & s \leq s_0 \end{cases} \quad (16)$$

$$wb_{DFC}(s) = \begin{cases} \dfrac{\eta_{DFC}\left(\frac{s-s_0}{S}\right)^2}{1 + \left(\frac{s-s_0}{S}\right)^2}, & s > s_0, \\ 0, & s \leq s_0 \end{cases} \quad (17)$$

where S is the maximal decomposition level, and S=10 in our case. s=0, 1, . . . , S is the level index. For multiple sub-bands within a certain level, the same weighting factor is used.

$\eta_{AC}$, $\eta_{DPC}$ and $\eta_{DFC}$ are the image type related constants controlling the values of the weighting factors and therefore they weight the contributions of each image type to the fusion image. It is clear that the factors for AC image are decreasing with s increasing, while those of DPC and DFC are increasing, resulting in higher frequency components to be preferred. $s_0$ represents the cutting frequency, which means that levels below $s_0$ are not used in the fusion. This applies to DPC and DFC images. Smaller $s_0$ means more low frequency information from DPC and DFC are involved in the fusion image, however it has been found to affect the appearance of the fusion image significantly and to make the fusion image un-interpretable by the radiologists.

$\eta_{AC}=0$ means all the information from the AC image is kept, while $\eta_{AC}>0$ gives preferences to the low frequency components of AC image. The loss of the high frequency components could be compensated by merging the high frequency components of the DPC image and helps suppress the total noise Error! Reference source not found. Eq. (16) and Eq. (17) are similar, however $\eta_{DPC}>\eta_{DFC}$ would mean DPC image is preferred to DFC image, and vice versa. In this paper, the contributions of the DPC image are preferred because the edge enhancement effects indeed improved the visual detection of many features at the level of diagnosis. Further, the DFC image contributes most to the noise in the three signals, therefore $n_{DFC}$ is chosen to be smaller than $\eta_{DPC}$, and accordingly will influence the final, fusion image less.

It is noted here that the strategy for choosing the band weighting factors could be very different according to different clinical scenarios and is not limited by Eq. (15)-(17). In practice, multiple weighting factor tables could be pre-stored, selected and used to generate the fusion image "on-the-fly", which gives the possibilities to tune the fusion image in diagnostic practices.

Global Noise Constraint

During the development of the algorithm it was observed that the noise level of the fusion image is mainly affected by the weighting on the bands and not by the pixel-wise weighting of the intra-band processing. To suppress the noise or at least keep its level similar to that of the AC image, a band-level weighting factor is assigned to each band.

For each band, the same noise estimation method described above is adopted. The average noise variance $\bar{\sigma}_{AC,l}$ of AC image for band l is given by $$\bar{\sigma}_{AC,l} = \sqrt{\frac{1}{N} \sum \sigma_{Nw}^2(i)}.$$

The same rule applies for DPC and DFC images.

The noise-constraint weighting factors are then given by $$wn_{AC,l} = \frac{1/\bar{\sigma}_{AC,l}}{1/\bar{\sigma}_{AC,l} + 1/\bar{\sigma}_{DPC,l} + 1/\bar{\sigma}_{DFC,l}} \quad (18)$$

$$wn_{DPC,l} = \frac{\bar{\sigma}_{AC,l}}{\bar{\sigma}_{DPC,l}} \times wn_{AC,l}$$

$$wn_{DFC,l} = \frac{\bar{\sigma}_{AC,l}}{\bar{\sigma}_{DFC,l}} \times wn_{AC,l},$$

for AC, DPC, DFC images, respectively.

Intuitively, the weighting factor is inverse proportional to the average noise level of the sub-band. By doing this, the noise level in the fusion image can be suppressed.

The image fusion scheme according to the present invention was evaluated by experimental MammoDPC data. The data was taken with a Talbot-Lau grating interferometer installed at Paul Scherrer Institute in Villigen, Switzerland. The interferometer was operated at the 5th Talbot distance, at a tube voltage of 40 kVp with mean energy of 28 keV and at a current of 25 mA.

Image Fusion Parameters

The detector noise related coefficients were measured, where $f^r=0.33$ and $f^s=0.27$. The spatial noise variances of the three signals were calculated according to Eq. (3). Decimated wavelets decomposition with Daubechies filters with order 4 was used. The size of three images was 7000(H)×5000(W). The images were decomposed into 10 levels, and each level contained three bands (LH,HL,HH) except the low frequency level LL.

Figure 4:
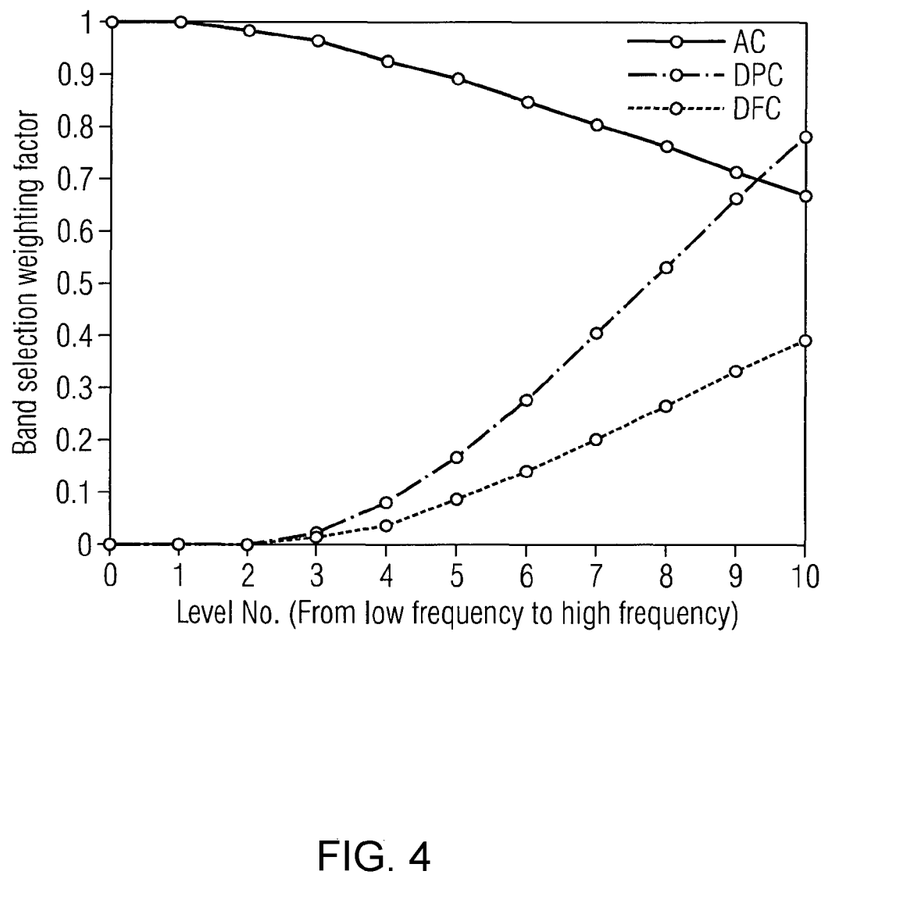
FIG. 4 shows quantitatively the band selection weighting factors used in the image fusion algorithm.

The band selection weighting factors were decided according to Eq. (15)-(17), where $\eta_{AC}=0.5$, $\eta_{DPC}=2$, $\eta_{DFC}=1$, and $s_0=2$ were used. These weighting factors are shown in FIG. 4. Band No. 0 represents the LL band (the "zero" frequency component).

Figure 5:
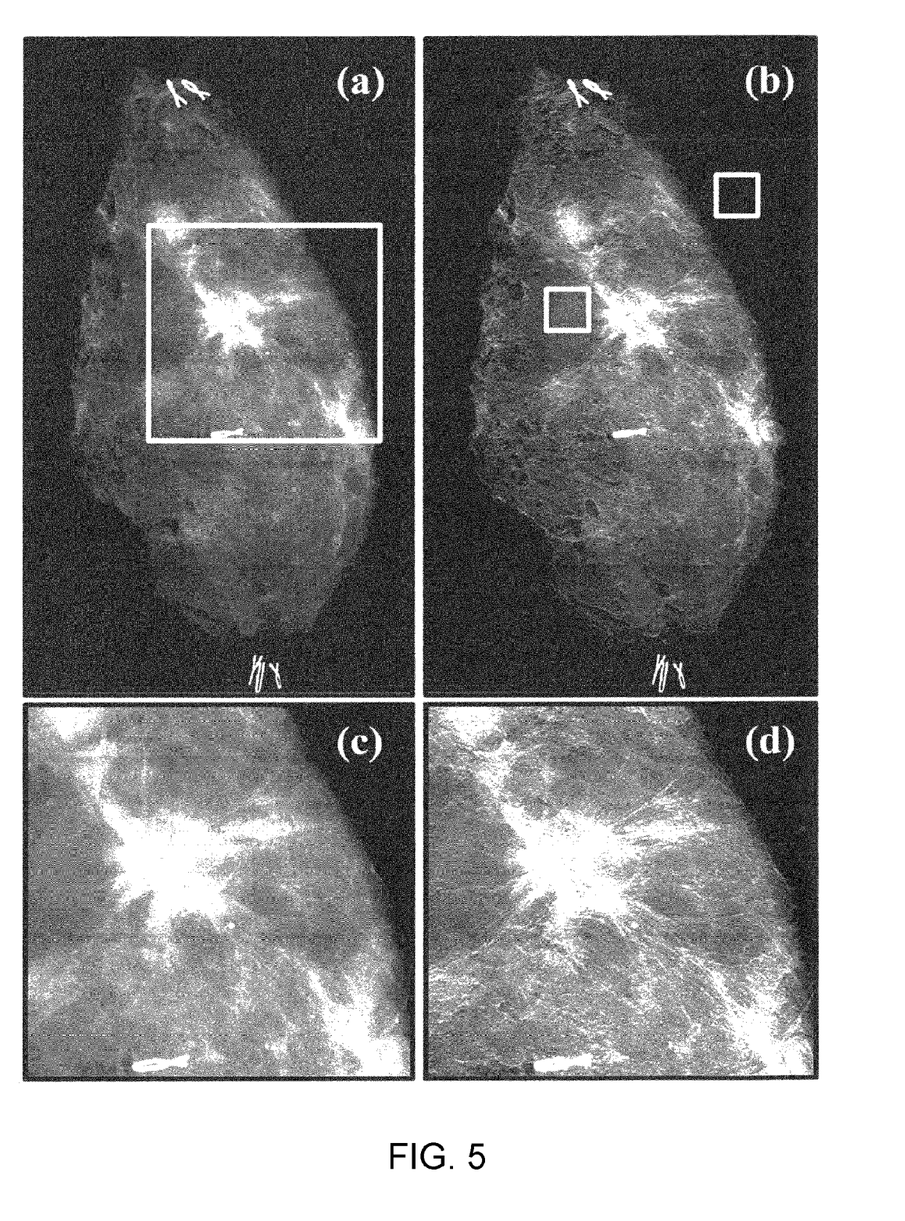
FIG. 5 shows the comparison of the fusion image and the AC image of a patient with a large tumor mass and spiculations; (a) is the AC image of the whole breast; (b) is the corresponding fusion image; (c) are the details of the ROI shown in the AC image; and (d) is the same ROI of the fusion image in details.

A fusion example using the proposed scheme is given in FIG. 5. The breast of this patient contains a large tumor mass and many spiculations. As it can be seen, the fusion image shows an overall better performance than the AC image in terms of sharpness and detail visibility. The fusion scheme clearly enhances the spiculations which are more obviously seen in the ROIs shown by FIGS. 5(c) and 5(d). Diagnostically, this enhancement is very relevant since spiculations are usually appearing in relation to malignant formations sometimes difficult to detect in normal, absorption based mammogram. Some air bubbles artefacts are more obvious in the fusion image, however this are related to the intrinsically ex-vivo character of the experiment and will disappear once in-vivo experiment will be performed. Therefore, removing those artifacts is not an issue and will not be discussed further.

FIG. 5 shows the comparison of the fusion image and the AC image of a patient with a large tumor mass and spiculations. (a) The AC image of the whole breast; (b) The corresponding fusion image; (c) The details of the ROI shown in the AC image; (d) The same ROI of the fusion image in details. The images are shown with the same display window. Note also that both images have been acquired with the same dose.

Evaluation of an image fusion method is a tough topic and there are no standard metric and/or method available. The evaluation strongly depends on the applications themselves. Here, two ROIs (a uniform area within the sample and one in the background), estimated the noise properties and compared the fusion image and the AC image to evaluate the noise property of the proposed fusion scheme. The two ROIs are indicated in FIG. 5(b). The mean and standard variance of the ROI within the sample are 0.913±0.008 in the AC image and 0.913±0.010 in the fusion image, respectively. For the ROI in the background, the values are 0.038±0.111 in the AC image, and 0.039±0.110 in the fusion. This rough qualitative analysis shows that the noise level in the fusion image was well preserved.

Figure 6:
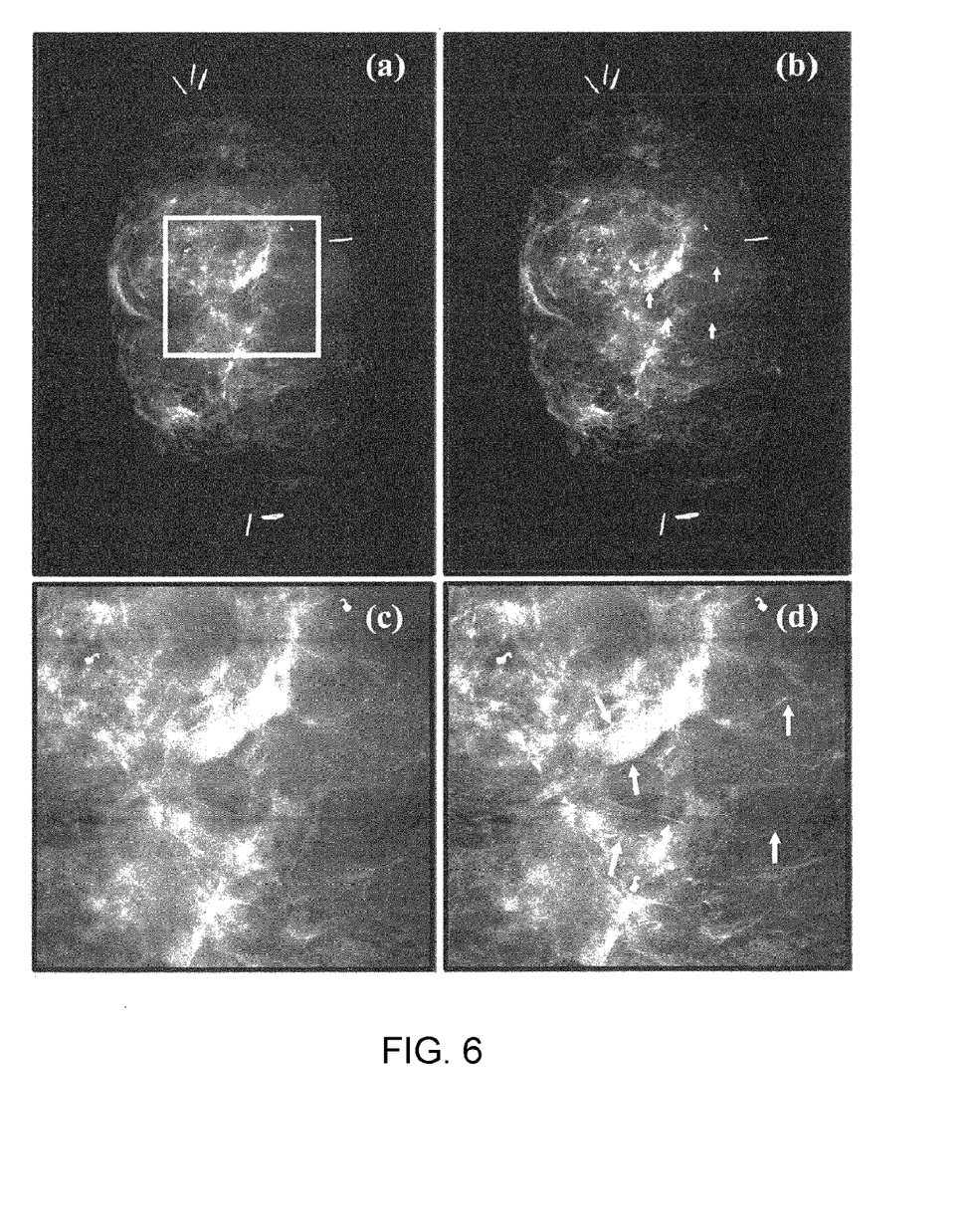
FIG. 6 shows the comparison of the fusion image and the AC image of a patient with irregular parenchyma; (a) is the AC image of the whole breast; (b) is the corresponding fusion image; (c) show the details of the ROI shown in the AC image; and (d) shows the same ROI of the fusion image in details.

Another example is shown in FIG. 6. This patient shows an irregular parenchyma because of a previous bilateral breast reduction mammoplasty. The diagnostic challenge was to distinguish invasive tumor from scar tissue. The microscopic structure of the scars was expected to generate a larger scattering signal than normal breast tissue. These enhanced tissue features contributed by the DFC images (as indicated by the arrows in FIG. 6(b)) are effectively merged into the fusion image, which provide complementary and useful information for diagnosis. FIG. 6 shows the comparison of the fusion image and the AC image of a patient with irregular parenchyma. (a) The AC image of the whole breast; (b) The corresponding fusion image. (c) The details of the ROI shown in the AC image; (d) The same ROI of the fusion image in details. The enhanced details in the fusion image are pointed out by arrows. The images are shown with the same display window.

CONCLUSION

The effective image fusion scheme for grating-based differential phase contrast mammography (MammoDPC) with the MR framework according to the present invention has been demonstrated. Higher frequencies of the DPC and DFC images are efficiently merged into the AC image, while noise is constrained. Future work will include the image quality evaluation with clinical practices and fusion parameter optimization for different applications.

REFERENCES

[1] M. Stampanoni, Z. Wang, T. Thuering et al., *The first analysis and clinical evaluation of native breast tissue using differential phase-contrast mammography*, Invest. Radiol. 46 (2011) 801.
[2] G. Piella, *A general framework for multiresolution image fusion: from pixels to regions*, Information fusion 4 (2003) 259.
[3] C. Clavijo, Z. Wang and M. Stampanoni, *Wavelet-based noise model driven denoising algorithm for differential phase contrast mammography*, Opt. Express 21 (2013) 10572.
[4] S. G. Chang, B. Yu and M. Vetterli, *Spatially adaptive wavelet thresholding with context modeling for image denoising*, IEEE Trans. Image Process. 9 (2002) 1522.

The invention claimed is:

1. A method for calculated image fusion in medical X-ray imaging, which comprises the steps of:
   merging absorption data, differential phase contrast data and small-angle scattering data of images of an underlying sample by a fusion algorithm into one single, grey-level image with enhanced details;
   basing the calculated image fusion on a multiple-resolution framework, where an original image is decomposed into several sub-images containing information of the original image at different spatial frequencies;
   obtaining the absorption data, the differential phase contrast data and the small-angle scattering data of the images from X-ray investigations based on grating-based interferometry, analyzer-crystal-based imaging, or coded aperture imaging, and using an arrangement for X-rays for obtaining quantitative X-ray images from a sample, the arrangement for X-rays containing:
      an X-ray source;
      at least two gratings; and
      a position-sensitive detector with spatially modulated detection sensitivity having a number of individual pixels;
   transforming the absorption data, the differential phase contrast data and the small-angle scattering data of the images into a multiple-resolution (MR) domain consisting of multiple levels (s denotes a level index), each level containing several sub-bands (o denotes a band index);
   processing and merging sub-band images in the MR domain by performing intra-band processing, inter-band processing or both the intra-band processing and the inter-band processing, wherein a fused sub-band $F_l(\hat{t})$ can be generally expressed by $$F_l(\hat{t}) = \sum_{X \in [AC,DPC,DFC]} wn_{X,l} \cdot wb_{X,l} \cdot w_{X,l}(\hat{t}) \cdot D_{X,l}(\hat{t}),$$

where X represents one of possible image types: an absorption contrast (AC), a differential phase contrast (DPC) or a dark-field contrast (DFC);
$D_{X,l}(\hat{t})$ represents an unprocessed coefficients of band l;
l denotes a pair (s,o), indicating a certain band at level S and of band o, o∈{HL,LH,HH} when a wavelet transform is used for a decomposition;

$\hat{t}=(m,n)$ denotes 2D coordinates in a sub-band image:
   the intra-band processing, which is represented by $w_{X,l}(\hat{t}) \cdot D_{X,l}(\hat{t})$, assigns a weighting factor $w_{X,l}(\hat{t})$ to each coefficient within the band l to increase a local signal-to-noise ratio;
   the inter-band processing gives a global weighting factor $wn_{X,l} \cdot wb_{X,l}$ to each band for selecting useful information according to image characteristics and constraining a global noise level; and
   $wb_{X,l}$ denotes a band selection weighting factor and $wn_{X,l}$ denotes a noise constraint weighting factor; and
   reconstructing a merged image by an inverse multiple-resolution transform.

2. The method according to claim 1, wherein the weighting factor $w_{X,l}(\hat{t})$ in the intra-band processing is possibly given by $$w_{X,l}(\hat{t}) = \phi\left(\frac{\sigma_{Sw}^{(s,o)}(\hat{t})}{\sigma_{Nw}^{(s,o)}(\hat{t})}\right),$$

where φ(x) is a linear function which normalizes x into a certain range wherein a ratio $$\frac{\sigma_{Sw}^{(s,o)}(\hat{t})}{\sigma_{Nw}^{(s,o)}(\hat{t})}$$

is defined as the local SNR for $D_{X,l}(\hat{t})$ and $\sigma_{Sw}^{(s,o)}(\hat{t})$ and $\sigma_{Nw}^{(s,o)}(\hat{t})$ denote a local estimated signal strength and a local standard noise variance, respectively; for simplicity, superscript (s,o) of $\sigma_{Sw}^{(s,o)}(\hat{t})$ and $\sigma_{Nw}^{(s,o)}(\hat{t})$ is omitted; $\sigma_{Sw}(\hat{t})$ and $\sigma_{Nw}(\hat{t})$ are used in the following claims; the three images types and their sub-bands are treated in a same way, so subscript X,l is also dropped.

3. The method according to claim 2, wherein the local standard noise variance $\sigma_{Nw}(\hat{t})$ in the MR domain is estimated using prior knowledge of a spatial pixel-wise noise variance $\sigma_{Ns}(\hat{t})$ in the original image:

$$[\sigma_{Nw}^{(s,o)}(\hat{t})]^2 \approx \frac{1}{2\pi}\int_{-\pi}^{\pi}|H^{(s,o)}(\hat{\omega})|^2 \cdot |A(\hat{\omega})|^2 e^{j\hat{\omega}\hat{t}}d\hat{\omega},$$

where $H^{(s,o)}(\omega)$ is a frequency response of cascaded wavelet filters at scale s and orientation o, for example $H^{(s,o)}(\omega) = \Pi_{i=0}^{s-1} H(2^i \omega)G(2^s \omega)$, where G(ω) and H(ω) are scaling and wavelet filters, respectively wherein the standard wavelet notation has been used:
A(ω̂) is the Discrete-time Fourier transform (DTFT) of $\sigma_{Ns}(\hat{t})$, that is $A(\hat{\omega}) = \int \sigma_{Ns}(\hat{t})e^{-j\hat{\omega}\hat{t}}d\hat{t}$; and $\sigma_{Ns}(\hat{t})$ is measured and/or calculated in advance.

4. The method according to claim 2, wherein:
   the local estimated signal strength $\sigma_{Sw}^{(s,o)}(\hat{t})$ represents a weight of the coefficient $D(\hat{t})$;
   $\sigma_{Sw}(\hat{t})$ is the local $l_p$ norm of the N neighbor coefficients of $D(\hat{t})$, which is $$\sigma_{Sw}(\hat{t}) = \left(\sum_{i \subseteq N}[D(\hat{t})]^p\right)^{1/p},$$

where $D(\hat{i})$ may include $D(\hat{t})$ itself or neighbor coefficients from its parent band (s−1,o) or son band (s+1,o);

a dedicated estimation of $\sigma_{Sw}(\hat{t})$ is achieved by Context Modeling, where $\sigma_{Sw}(\hat{t})$ is determined as following:

(i) a context $Z(\hat{t})$ is assigned to each said coefficient $D(\hat{t})$, which indicates a significance of the coefficient and is defined as a weighted average of absolute values of the N neighbor coefficients of $D(\hat{t})$:

$$Z(\hat{t}) = w^T u_t,$$

where w and $u_t$ are a vectorized N×1 weighting factor and vectorized absolute values of the N neighbor coefficients;

(ii) The weighting factor w is statistically obtained by least-square estimation through a whole sub-band:

$$w = (U^T U)^{-1} U^T |D|,$$

where U is a M×N matrix with each row being $u_t^T$ for all $\hat{t}$ and D is the M×1 vector containing all the coefficients $D(\hat{t})$, M is a number of the coefficients in the sub-band;

(iii) After $Z(\hat{t})$ is decided for each coefficient, coefficients whose contexts $Z(\hat{t})$ are close in value are located and sorted;

Let $B_t$ denotes a set of coefficients $\{D(\hat{t})\}$ whose context falls in a similar value range, those coefficients are considered to have similar significances and their standard variance $\sigma_{Sw}$ gives a measurement of the significance, $$\sigma_{Sw}(\hat{t}) = \sqrt{\max\left(\frac{1}{L}\sum_{B_t} D(\hat{t})^2 - \sigma_{Nw}^2(\hat{t}), 0\right)},$$

where L is the number of the coefficients in $B_t$.

5. The method according to claim 1, wherein the band selection weighting factors is $$wb_{AC,l}(s) = \frac{1}{1 + \eta_{AC}\left(\frac{s}{S}\right)^2},$$

$$wb_{DPC,l}(s) = \begin{cases} \frac{\eta_{DPC}\left(\frac{s-s_0}{S}\right)^2}{1+\left(\frac{s-s_0}{S}\right)^2}, & s > s_0 \\ 0, & s \le s_0 \end{cases}$$

$$wb_{DFC,l}(s) = \begin{cases} \frac{\eta_{DFC}\left(\frac{s-s_0}{S}\right)^2}{1+\left(\frac{s-s_0}{S}\right)^2}, & s > s_0 \\ 0, & s \le s_0 \end{cases}$$

where S is a maximal decomposition level and s=0, 1, . . . , S is a level index;

for multiple sub-bands within a certain level, a same weighting factor is used;

$\eta_{AC}$, $\eta_{DPC}$ and $\eta_{DFC}$ are an image type related constants controlling values of the weighting factors and therefore weighting contributions of each image type to the fusion image; and $s_0$ represents a threshold frequency.

6. The method according to claim 1, wherein global noise constraint weighting factors are inversely proportional to an average noise level of a sub-band; for instance, $$wn_{AC,l} = \frac{1/\overline{\sigma}_{AC,l}}{1/\overline{\sigma}_{AC,l} + 1/\overline{\sigma}_{DPC,l} + 1/\overline{\sigma}_{DFC,l}}$$

$$wn_{DPC,l} = \frac{\overline{\sigma}_{AC,l}}{\overline{\sigma}_{DPC,l}} \times wn_{AC,l}$$

$$wn_{DFC,l} = \frac{\overline{\sigma}_{AC,l}}{\overline{\sigma}_{DFC,l}} \times wn_{AC,l},$$

where $\overline{\sigma}_{AC,l}$ is an average noise variance of AC image at band l, $$\overline{\sigma}_{AC,l} = \sqrt{\frac{1}{N}\sum \sigma_{Nw}^2(\hat{t})};$$

and for a DPC and DFC image, $\overline{\sigma}_{DPC,l}$ and $\overline{\sigma}_{DFC,l}$ are decided in a same way.

7. The method according to claim 1, wherein the arrangement for X-rays further comprising:

a processing device to record the images of the position-sensitive detector;

the processing device evaluating intensities for each pixel in a series of images, in order to identify characteristics of an object for each individual pixel as one of an absorption dominated pixel, a differential phase contrast dominated pixel, or an X-ray scattering dominated pixel; and wherein a series of images is collected by continuously or stepwise rotating from 0 to π or 2π either the sample or the arrangement and the x-ray source relative to the sample.

8. The method according to claim 7, wherein the at least two gratings include a first grating being a line grating selected from the group consisting of an absorption grating and a phase grating, wherein the phase grating is a low absorption grating but generating a considerable X-ray phase shift, the phase grating being of π or odd multiples thereof.

9. The method according to claim 8, wherein:

the at least two gratings include a second grating being a line grating having a high X-ray absorption contrast with its period being a same as that of a self image of the first grating; and the second grating being placed closely in front of the position-sensitive detector, or integrated in it, with its lines parallel to those of the first grating.

10. The method according to claim 9, which further comprises performing phase stepping by a shift of one of the gratings with respect to other ones of the gratings in a direction perpendicular to an orientation of grating lines of the first and the second gratings.

11. The method according to claim 7, which further comprises applying a fusion protocol to multiple angular projections acquired with a purpose of performing a tomographic reconstruction.

12. The method according to claim 7, wherein a presented fusion protocol is applied to tomographically reconstructed slices.

13. The method according to claim 1, wherein the images are taken according to a so-called "near field regime" or according to a "Talbot-regime".

14. The method according to claim 13, wherein for a near-field-regime operation, a distance between the gratings is chosen freely within the near field regime, and for the Talbot-regime is chosen according to $$D_{n,sph} = \frac{L \cdot D_n}{L - D_n} = \frac{L \cdot n \cdot p_1^2 / 2\eta^2 \lambda}{L - n \cdot p_1^2 / 2\eta^2 \lambda}$$

where $n = 1, 3, 5 \ldots$, and $$\eta = \begin{cases} 1 & \text{if the phase shift of } G_1 \text{ is } (2l-1)\frac{\pi}{2}, \quad p_2 = \frac{L + D_{n,sph}}{L} p_1 \\ 2 & \text{if the phase shift of } G_1 \text{ is } (2l-1)\pi, \quad p_2 = \frac{L + D_{n,sph}}{L} \frac{p_1}{2} \end{cases},$$

where $l=1, 2, 3 \ldots$, $D_n$ is an odd fractional Talbot distance when a parallel X-ray beam is used, while $D^{n,sph}$ is that when a fan or cone X-ray beam is used, L is a distance between the X-ray source and the first grating.

15. The method according to claim 1, wherein the decomposing into the several sub-images is performed by one of Laplacian, wavelets or similar transformations to carry out the decomposition.

* * * * *